United States Patent [19]

Ostrea, Jr.

[11] Patent Number: 5,015,589
[45] Date of Patent: May 14, 1991

[54] METHOD FOR DETECTING MATERNALLY TRANSFERRED DRUG METABOLITES IN NEWBORN INFANTS

[75] Inventor: Enrique M. Ostrea, Jr., New Baltimore, Mich.

[73] Assignee: Board of Governors of Wayne State University, Detroit, Mich.

[21] Appl. No.: 264,131

[22] Filed: Oct. 28, 1988

[51] Int. Cl.$^5$ ............................................. G01N 33/00
[52] U.S. Cl. ..................................... 436/92; 436/816; 436/901; 436/93
[58] Field of Search .................... 436/93, 92, 816, 901

[56] References Cited

U.S. PATENT DOCUMENTS 4,771,005  9/1988  Spiro et al. ............................ 436/93

OTHER PUBLICATIONS

Ostrea, E. M. et al., Dev. Pharmacol. Therm., 1:163–170 (1988).
Ostrea, E. M. et al.,. Pediatr. Res. 17:153A (1983).
Ostrea, Jr., E. M. et al., "The Detection of Heroin, Cocaine and Cannabinoid Metabolites in the Stools of Infants of Drug Dependent Mothers: Clinical Significance", Pediatric Research, 1987: 21:240A.
Zelson, C. et al., Pediatrics, 48:178 (1971).
Ostrea et al., J. Pediatr, 88: 642–645 (1976).
Halstead et al., Clin. Biochem, 21: 59–61 (1988).
Ostrea et al., Dev Pharmacol. Ther., 1: 163–170 (1980).

*Primary Examiner*—David L. Lacey
*Assistant Examiner*—David Redding
*Attorney, Agent, or Firm*—Ian C. McLeod

[57] ABSTRACT

A method for detecting the presence of drug metabolites in the meconium of newborn infants is described. The method involves separation of the drug metabolites from meconium in solution and then assaying the solution for the presence of the drug metabolites. The method is particularly useful for detection of cocaine, morphine and cannabinoids; however, any drug metabolite in the infant meconium can be tested. Conventional assay methods are used for the drug metabolites in the solutions derived from the meconium. The method provides for early detection of drug presence in infants which contribute to infant illness.

8 Claims, No Drawings

METHOD FOR DETECTING MATERNALLY TRANSFERRED DRUG METABOLITES IN NEWBORN INFANTS

BACKGROUND OF THE INVENTION (1) Summary of the Invention

The present invention relates to a method for detecting drug metabolites which are transferred from a mother to a newborn infant during pregnancy. In particular, the method involves the isolation of meconium from a newborn infant, separation of the drug metabolites from the meconium in solution and assaying for the metabolites in the solution.

(2) Prior Art

The use of illicit drugs in the United States is widespread. According to a national survey in 1985, an estimated 23 million people were users of illicit drugs (1985 National Health Household Survey on Drug Abuse. Rockville, Md., 1987). Although exact figures are not known, a sizeable portion of drug users are women of childbearing age or are pregnant women. Infants born to these drug dependent women have multiple problems. In the neonatal period, their mortality rate is increased as well as morbidity, which includes asphyxia, prematurity, low birth weight, hyaline membrane disease, infections, aspiration pneumonia, congenital malformations, abnormal heart rate and breathing patterns and drug withdrawal (Ostrea E. M, Chavez C. J., Perinatal problems (excluding neonatal withdrawal) in maternal drug addiction: A study of 830 cases J. Pediatr 94:292–295 (1979); Zelson C, Rubio E, and Wasserman E., Pediatrics 48:178 (1971)). Long term sequelae are not uncommon and include delays in physical growth and mental development, sudden infant death syndrome, hyperactivity, ocular and neurologic abnormalities and lately, a risk to acquired immunodeficiency disease (Wilson, G. S., M. McCreary, J. Kean and J. Baxter, Pediatrics 63:135–144 (1979; Chavez, C. J., et al, J. Pediatrics 95:407–409 (1979); Chasnoff, I., J., et al, Pediatrics 70:210–213 (1982); Chavez, C. J., et al., Pediatr Res 12:367A (1979); and Oleske J., et al., J. Am. Med Assoc. 249:2345–2349 (1983)). At present, cocaine abuse among pregnant women has also become widespread and infant morbidity, notably cerebrovascular problems have been reported (Chasnoff, I. J., et al., J. Pediatr 108:456–459 (1986)). Because of these immediate and long term problems, infants of drug dependent women (IDDM) constitute a high risk group and have to be identified as soon as possible after birth if intervention is to be successful.

Unfortunately, such detection is not easy. Many of the drugs which the fetus was exposed to in utero, do not produce immediate or recognizable effects in the infant after birth which arouse suspicion (Kandall, S. R., Am. J. Dis Child 127:58–61 (1974)). Maternal admission of drug usage may not always be obtained because of fear of the consequences associated with such admittal. Even with maternal cooperation, the experience has been that the information volunteered by the mother regarding the type and frequency of her drug usage can be inaccurate (Ostrea, E. M., et al., J. Pediatr 88:642–645 (1976)). Lastly, the infant's urine is routinely screened for drugs; however, there is a high rate of false negative results with this method (Halstead, A. C., et al., Clin. Biochem. 21:59–61 (1988)).

A previous study showed that the metabolites of morphine were found in high concentrations in the gstlointestines of the fetuses of morphine addicted monkeys (Ostrea, E. M., et al., Dev. Pharmacol. Ther., 1:163–170 (1980)). It was not appreciated that this result would serve as a basis for tests in humans for such drugs.

OBJECTS

It is therefore an object of the present invention to provide a method for testing for drug metabolites in infants. It is an object of the present invention to provide a method which is reliable. Further still, it is an object of the present invention to provide a method which is simple and economical to perform.

These and other objects will become increasingly apparent by reference to the following description.

GENERAL DESCRIPTION

The present invention relates to a method for detecting maternally transferred drug metabolites in a newborn infant which comprises: isolating meconium from the newborn infant which possibly contains the transferred drug metabolites from the mother; separating the drug metabolites in a solution from the meconium; and assaying the solution for the drug metabolites.

In particular the present method involves the detection of the drug metabolites in fecal meconium although it is possible to detect the metabolites in oral meconium. The oral meconium contains much less of the drug metabolites and therefore is less likely to produce reliable results.

The drug metabolites are provided in solution separated from the meconium. This is best accomplished by using a solvent extraction of the drug metabolites. Preferred solvents are water or water miscible organic solvents or mixtures thereof, although any solvent which is a non-solvent for the solid portions of the meconium can be used as is well known to those skilled in the art. Water is used as the solvent where the drug metabolites are cocaine and morphine. The methanol is preferably used where there are cannabinoid metabolites (marijuana and the like). Usually lower alkanols containing 1 to 6 carbon atoms can be used for metabolites of this kind.

Generally the solid portions of the meconium are separated by centrifugation. Other separation means, such as microfiltration, liquid chromatography and the like could be used. All of this is well known to those skilled in the art.

The aqueous solutions preferably are adjusted and have a pH between about 1.2 and 4.0 for the extraction of the drug metabolites from the meconium. Hydrochloric acid is preferred; however, other inorganic and organic acids can be used to lower the pH of the water so long as they do not interfere with the extraction or the subsequent assay.

Once the drug metabolites are separated from the meconium, standard assays are performed in order to determine the presence of the drug metabolites. These assays can be radioimmunoassays or ELISA type assays, using antibodies or other probes which are specific for the drug metabolite. Single antibody or multiple antibody sandwich assays can be used as is well known to those skilled in the art. Further still, other quantitative or qualitative chemical tests can be used to assay for the drug metabolites as is well known to those skilled in the art.

SPECIFIC DESCRIPTION

It was hypothesized that in the infants of drug dependent mothers (IDDM), a high concentration of drug metabolites would be detected in the infant's stools (meconium). Meconium from IDDM was analyzed for the metabolites of three commonly abused drugs, heroin, cocaine and cannabinoids. The drug metabolites were detected in meconium at higher frequency and concentration than in the infants' urine. It was concluded that the analysis of meconium for drugs provided a new and important tool to detect infants who have been exposed to drugs, in utero.

Meconium (first 3 day stools) obtained from 20 infants of drug dependent mothers (IDDM) and 5 control infants were analyzed by radioimmunoassay for the metabolites of 3 commonly abused drugs, heroin, cocaine and cannabinoids. The control stools did not show any drug. Meconium from the IDDM showed the presence of at least one drug metabolite: 80% of the IDDM showed cocaine (range$-0.14-19.91$ mcg/gm stool), 55% showed morphine (range$=0.41-14.97$ mcg/gm stool) and 60% showed cannabinoid (range$=0.05-0.67$ mcg/gm stool). The concentrations of metabolites were highest in the first 2 day stools; some stools tested positive up to the third day. In contrast, only 42% of the infants had a positive urine screen (fluorescent polarization immunoassay method). Paired urine and meconium, both analyzed by radioimmunoassay, showed a higher concentration of drug metabolites in the latter; 8 urine samples tested negative for drugs despite a corresponding positive stool test. We conclude that meconium is ideal for drug screen in the neonate. It contains a high concentration of drug metabolites which are detectable up to 2 to 3 days after birth.

METHODS

Meconium was collected for three days in 20 non-breast fed infants born to mothers who by history had abused drugs during pregnancy, commonly heroin, cocaine, methadone, cannabinoids, amphetamines, barbiturates and benzodiazepines. The extent and frequency of drugs used, however, in these women was difficult to ascertain from the history alone. The stools were obtained directly from the diaper and pooled and labelled for each day. Each drug dependent infant also had a first day urine specimen sent for routine drug testing. The latter employed the TDx TM system which is a fluoresence polarization immunoassay developed by Abbott Laboratories (Abbott Lab Diagnostic Division, P.O. Box 152020, Irving, Tex. 5015-2020). In 5 infants, paired stool and urine samples were also obtained. The urine was collected using an infant urine collector once every morning for 3 days. Care was taken to ensure that the urine samples were not contaminated with stools. Only non-contaminated urine samples were analyzed. Unlike the stools, 3 days of continuous collection of urine was not done due to the problem of skin excoriation with the procedure.

Stools were also collected as in the above, each day for three days in infants who were born to women who were known, by history, not to have used drugs during pregnancy (control). In 2 of these infants, paired urine and stool samples were also obtained. All stool and urine specimens were frozen at $-23°$ C. until the day of analysis.

To assay for drug metabolites in meconium, about 0.5 and 1.0 g of the specimen was weighed. Ten (10) mL of distilled water and 1 mL of concentrated HCL was added to the stool and homogenized with a vortex stirrer. The mixture was filtered through glass wool to remove gross particulate matter. The filtrate was centrifuged at 9770 g for 10 min. An aliquot of the supernate was tested for morphine and cocaine metabolites by radioimmunoassay (see below). To assay for cannabinoid metabolites, about 0.1 g of meconium was weighed to which was added 0.4 mL of absolute methanol. The sample was mixed in a vortex stirrer and allowed to stand in room temperature for 10 minutes. The mixture was centrifuged at 9770 g for 10 minutes. An aliquot of the supernate was tested for cannabinoid metabolites by radioimmunoassay.

To assay the urine for drug metabolites, the urine volume was first measured. One (1) mL of concentrated HCl was added. The mixture was centrifuged at 9770 g for 10 minutes. An aliquot of the supernate was tested for morphine, cocaine and cannabinoid metabolites by radioimmunoassay.

Animal Studies

Four timed pregnant Wistar rats were studied. Three of the rats were given daily doses of one of the following drugs: cocaine hydrochloride (50 mg/kg/day, subcutaneously, once daily, for 10 days), morphine hydrochloride (50 mg/kg/day, subcutaneously, once daily, for 12 days) or cannabinoid (Dronabinol 25 mg/kg/day, in sesame seed oil, administered by oral intubation, once daily, for 12 days). The drugs were started on the 8th or 10th day of gestation to avoid significant fetal losses which occur when these drugs are given early in pregnancy. One rat did not receive any drug throughout pregnancy and served as the "control". To prevent the pups from breast feeding, the dams were sacrificed on the 20th day of gestation and the pups were delivered by cesarean section. The dams were sacrificed using carbon dioxide gas and immediately after death, the pups from each dam were delivered through an abdominal incision. The small and large intestines of the pups were harvested, externally washed of blood with 0.9% NaCl, dry blotted, collectively weighed and then frozen until the time of analysis.

To assay the intestinal contents for drug metabolites, the pups' intestines were thawed. Approximately 0.5 grams of tissue was weighed and homogenized in 10 ml of distilled water using a metal stirrer. One (1) ml of concentrated HCl was added to the homogenate. The homogenate was filtered through glass wool and then centrifuged at 9770 g for 10 minutes. The supernate was analyzed for morphine and cocaine metabolites by radioimmunossay. To assay for cannabinoid metabolites, approximately 0.1 g of intestines was weighed to which was added 0.4 mL of absolute methanol. The sample was homogenized using a metal stirrer and then allowed to stand at room temperature for 10 minutes. The homogenate was centrifuged at 9770 g for 10 minutes. An aliquot of the supernate was assayed for cananbinoid metabolites by radioimmunoassay.

Radioimmunoassay of the supernates for the metabolites of heroin, cocaine and cannabinoids were done using the Abuscreen TM (Roche Diagnostic Systems, Nutley, N.J.) kits following the manufacturer's instructions. These kits have high specificity for the drug metabolites being tested. The following metabolites were identified: cocaine (benzoylecgonine), heroin (morphine and morphine glucuronide) and cannabinoids (11 nor delta 9 THC 9-carboxylic acid). Radioactivity was quantified using a TriCarb gamma scintillation counter (Packard Instrument Co., Downers Grove, Ill).

RESULTS

The control stools did not show any drug metabolite as shown in Table 1. Meconium from the IDDMs showed the presence of at least one drug metabolite: 80% (16/20) of the IDDMs tested showed cocaine (range=0.14–19.91 mcg/g stool); 55% (11/20) showed morphine (range—0.41–14.97 mcg/g stool) and 60% (12/20) showed cannabinoid (range—0.05–0.67 mcg/g stool) metabolites. The stools were positive for drugs up to the third day of sampling; in general, the number of stools positive for drug metabolites and their metabolite concentrations were highest during the first two days. In contrast, the routine urine drug screen on the infants by the TDx ™ system showed that only 8 out of the 19 IDDMs tested (42%) were positive for drugs. Furthermore, in each positive test, only one drug was identified, usually corresponding to the drug which had the highest concentration in the stools.

In paired urine and stool specimens analyzed by radioimmunoassay, more drug metabolites were isolated from meconium and at higher concentrations than in the urine as shown in Table 2. Eight urine samples tested negative for drugs (predominantly cannabinoids) despite a positive test in the stools.

The results of the animal studies are presented in Table 3. The drug metabolites corresponding to the specific drugs that the dams received were recovered from the pups' intestines.

DISCUSSION

The metabolites of three commonly abused drugs, morphine, cocaine and cannabinoids can be recovered in significant concentrations from the meconium of drug dependent infants. Animal studies further confirmed these findings. The following is an explanation for these observations. Meconium is a repository of the metabolites of drugs which the fetus was exposed to, in utero. Drugs of abuse in humans are commonly metabolized by the liver into water soluble derivatives (Jaffe, J., Drug addiction and drug abuse.

TABLE 1

Recovery of Drug Metabolites in the Meconium of Drug Dependent Infants

| | COCAINE (ug/gm) stool | | | MORPHINE (ug/gm) stool | | | CANNABINOID (ug/gm) stool | | | URINE SCREEN* |
|---|---|---|---|---|---|---|---|---|---|---|
| | Day 1 | Day 2 | Day 3 | Day 1 | Day 2 | Day 3 | Day 1 | Day 2 | Day 3 | |
| I. CONTROL INFANTS (n = 5) | | | | | | | | | | |
| 1. B.L. | (−) | (−) | (−) | (−) | (−) | (−) | (−) | (−) | (−) | |
| 2. B.A. | (−) | (−) | (−) | (−) | (−) | (−) | (−) | (−) | (−) | |
| 3. B.C. | (−) | (−) | (−) | (−) | (−) | (−) | (−) | (−) | (−) | |
| 4. B.D. | (−) | (−) | (−) | (−) | (−) | (−) | (−) | (−) | (−) | |
| 5. B.A. | (−) | (−) | (−) | (−) | (−) | (−) | (−) | (−) | (−) | |
| II. DRUG DEPENDENT INFANTS (n = 20) | | | | | | | | | | |
| 1. B.H. | 6.35 | 3.23 | (−) | 3.28 | 1.72 | 0.56 | (−) | (−) | (−) | (−) |
| 2. B.R. | 2.34 | 2.17 | 1.17 | 1.19 | 1.17 | (−) | (−) | (−) | (−) | (−) |
| 3. B.W. | 1.77 | 9.68 | 3.67 | (−) | (−) | (−) | (−) | (−) | (−) | (−) |
| 4. B.D. | 10.86 | 11.29 | (−) | (−) | (−) | (−) | 0.13 | 0.29 | (−) | (−) |
| 5. B.W. | (−) | (−) | (−) | 5.38 | 12.11 | (−) | 0.05 | (−) | (−) | opiates |
| 6. B.S. | 4.54 | 17.78 | 1.03 | (−) | (−) | (−) | 0.34 | 0.66 | (−) | cocaine |
| 7. B.P. | (−) | (−) | (−) | 0.69 | 0.97 | 0.54 | (−) | (−) | (−) | (−) |
| 8. B.G. | 2.39 | 2.16 | 1.07 | 3.75 | 2.43 | 2.31 | (−) | (−) | (−) | (−) |
| 9. B.W. | 5.40 | 8.41 | 0.41 | (−) | (−) | (−) | (−) | (−) | 0.09 | cocaine |
| 10. B.T. | (−) | (−) | ns | 11.74 | 14.97 | ns | (−) | (−) | ns | opiates |
| 11. B.A. | (−) | (−) | (−) | (−) | (−) | (−) | 0.06 | 0.09 | (−) | cannabinoid |
| 12. B.L. | 11.48 | 0.41 | (−) | (−) | (−) | (−) | 0.13 | (−) | (−) | cocaine |
| 13. B.C. | 7.40 | 6.70 | ns | 5.36 | 5.73 | ns | 0.48 | 0.37 | ns | cocaine |
| 14. B.M. | 11.42 | 0.29 | ns | 6.95 | 0.73 | ns | 0.67 | (−) | ns | (−) |
| 15. B.M. | 3.29 | 19.91 | 6.10 | (−) | (−) | (−) | (−) | (−) | (−) | ns |
| 16. B.N. | 0.26 | (−) | ns | 2.26 | 0.77 | ns | 0.14 | (−) | ns | (−) |
| 17. B.U. | 1.76 | 3.52 | 2.42 | 1.24 | 1.21 | 1.24 | (−) | (−) | 0.12 | (−) |
| 18. B.S. | ns | 16.23 | 13.15 | ns | 0.41 | (−) | ns | 0.22 | 0.09 | cocaine |
| 19. B.J. | 0.95 | 0.14 | (−) | (−) | (−) | (−) | 0.07 | (−) | (−) | (−) |
| 20. B.T. | 0.06 | 0.03 | (−) | (−) | (−) | (−) | 0.19 | 0.17 | 0.05 | (−) | ns - no sample
*urine drug screen by TDx System (Abbott Laboratories)

TABLE 2

Identification by Radioimmunoassay of Drug Metabolites in the Urine vs Stools of Drug Dependent Infants

| | | COCAINE (ug/gm or ml) | | | MORPHINE (ug/gm or ml) | | | CANNABINOID (ug/gm or ml) | | |
|---|---|---|---|---|---|---|---|---|---|---|
| | | DAY 1 | DAY 2 | DAY 3 | DAY 1 | DAY 2 | DAY 3 | DAY 1 | DAY 2 | DAY 3 |
| I. CONTROL INFANTS (n = 2) | | | | | | | | | | |
| 1. B.Ab. | Urine | (−) | (−) | (−) | (−) | (−) | (−) | (−) | (−) | (−) |
| | Stool | (−) | (−) | (−) | (−) | (−) | (−) | (−) | (−) | (−) |
| 2. B.A. | Urine | (−) | (−) | (−) | (−) | (−) | (−) | (−) | (−) | (−) |
| | Stool | (−) | (−) | (−) | (−) | (−) | (−) | (−) | (−) | (−) |
| II. DRUG DEPENDENT INFANTS (n = 5) | | | | | | | | | | |
| 1. B.W. | Urine | (−) | (−) | (−) | 0.85 | 0.64 | 0.17 | (−) | (−) | (−) |
| | Stool | (−) | (−) | (−) | 5.38 | 12.11 | (−) | 0.48 | (−) | (−) |
| 2. B.S. | Urine | >0.95 | >0.95 | >0.95 | (−) | (−) | (−) | (−) | (−) | (−) |
| | Stool | ns | 16.23 | 13.15 | ns | 0.41 | (−) | ns | 0.22 | 0.09 |

TABLE 2-continued

Identification by Radioimmunoassay of Drug Metabolites in the Urine vs Stools of Drug Dependent Infants

| | | COCAINE (ug/gm or ml) | | | MORPHINE (ug/gm or ml) | | | CANNABINOID (ug/gm or ml) | | |
|---|---|---|---|---|---|---|---|---|---|---|
| | | DAY 1 | DAY 2 | DAY 3 | DAY 1 | DAY 2 | DAY 3 | DAY 1 | DAY 2 | DAY 3 |
| 3. B.J. | Urine | 0.23 | 0.05 | 0.05 | (—) | (—) | (—) | (—) | (—) | (—) |
| | Stool | >0.95 | 0.14 | (—) | (—) | (—) | (—) | 0.07 | (—) | (—) |
| 4. B.T. | Urine | 0.03 | (—) | (—) | (—) | (—) | (—) | 0.02 | (—) | (—) |
| | Stool | 0.06 | 0.03 | (—) | (—) | (—) | (—) | 0.19 | 0.17 | 0.04 |
| 5. B.W. | Urine | >0.95 | >0.95 | >0.95 | (—) | (—) | (—) | (—) | 0.04 | (—) |
| | Stool | 5.40 | 8.41 | 0.41 | (—) | (—) | (—) | (—) | 0.09 | (—) | ns - no sample

TABLE 3

The Recovery of Drug Metabolites in the Intestines of Rat Pups Whose Mothers Received Drugs During Pregnancy

| Drug (route) | Dose | Rat Weight (gm) | No. of Pups | Drugs in Pups' Intestines (ug/gm) |
|---|---|---|---|---|
| 1. Control | 0 | 212 | 15 | 0.00 |
| 2. Cocaine HCl (s.c.) | 50 mg/kg × 10 days | 198 | 11 | 0.47 |
| 3. Morphine SO$_4$ (s.c.) | 50 mg/kg × 12 days | 216 | 13 | 1.36 |
| 4. Cannabinoid (oral) | 25 mg/kg × 12 days | 223 | 12 | 2.50 |

In: Goodman, L., Gillman, A., eds. The pharmacologic basis of therapeutics London: Collier-Macmillan, 1980:535–84 ) which are excreted either into the bile or urine (Woods, L. A., J. Pharmacol Exper. Ther. 112:154–75 (1954)). Uniquely in the fetus, drug metabolites whether excreted in the bile or urine eventually accumulate in the meconium; metabolites in the bile are deposited directly into the intestines, whereas those which are excreted in the urine, admix with the amniotic fluid and are reingested by the fetus. Likewise, the fetus does not normally defecate in utero. Thus, meconium represents an excretion product which is cumulative of the entire gestation. Overall therefore, meconium acts as a reservoir of drug metabolites in the fetus; seemingly a stockpile of pharmacologic waste products throughout gestation.

The detection of drug metabolites in meconium offers a number of clinical considerations. Foremost is the use of meconium for drug screening. The drug screen using the infant's urine has its limitations since the successful detection of drug metabolites in urine depends on the timing of the last drug intake by the mother or when the urine of the infant was collected (Halstead, A. C., et al., Clin. Biochem 21:59–61 (1988)). A high rate of false negative results has therefore been observed. Our experience verifies this diagnostic problem. Urine from 337 infants of known drug dependent mothers was tested by thin layer chromatography. It was found that only 13% were positive (Ostrea, E. M., et al., Pediatr Res. 17:153A (1983)). In the current comparative assays, only 42% of the urine samples taken from drug dependent infants were positive for drugs (Table 1) when tested by fluorescent polarization immunoassay. Even with more sensitive methods such as by radioimmunoasay, 8 urine samples tested negative for drugs despite a positive test in the stools. Clearly, there is a need for a better way to detect prenatal drug exposure in this high risk group of infants.

The analysis of meconium for drugs offers this alternative. As shown by the present invention, meconium is an ideal specimen for drug screen in the suspected neonate: it is easy to collect and compare to urine, it qualitatively and quantitatively contains more drugs which are detectable for as long as three days after birth (Tables 1 and 2). The latter should account for a higher success rate in drug detection particularly in the event that the infant was not tested early.

Meconium can also be analyzed for other drugs of abuse besides those tested in this study. Presumably, the method of extraction may differ for one class of drug to the other. For instance, it was found that to isolate cannabinoids from meconium, a prior extraction with methanol was required Likewise, meconium could be screened for the metabolites of licit drugs which have been used by the mother during pregnancy. Overall, meconium can potentially be used to comprehensively establish the drug profile by the mother throughout pregnancy, independent of her own history. This procedure, if validated will have distinct advantages over history taking.

Another area to consider is whether the drug metabolites which are found in high concentrations in meconium are reabsorbed by the fetus. The fetal gut is enriched with luminal beta glucuronidase (Antonowicz, I., et al., Gastroenterology 67:51–58 (1974)) which promote the hydrolysis and presumably, the reabsorption of drug substrates. This enterohepatic recirculation of drugs in the fetus, if actually present, can lead to the reexposure of the fetus to drugs, as well as influence the amount of drug metabolites that can be recovered from meconium for diagnostic purposes. To some extent, this possibility is suggested by the observed differences between the concentrations of drug mtabolites in meconium from days 1 to 3 (Table 1). Stools from day 3 have the lowest metabolite concentration since these stools represent a mixture of in utero as well as postnatally formed (non-drug exposed) stools. On the other hand, meconium passed during the first 2 days of life show high concentrations of drug metabolites since they represent stools which have been predominantly formed in utero and therefore exposed to the drugs which the fetus had metabolized. The varying concentrations of drug metabolites between the first and second day meconium may reflect the effect of reabsorption of drugs from meconium, the timing of fetal exposure to drugs, or both. Thus this method opens a further possibility of treatment of the infants to remove the meconium before readsorption.

It has been demonstrated that the metabolites of the drugs which the infant was exposed to in utero can be found in meconium in high concentrations. The clinical significance of these finds are discussed; foremost is the usefulness of meconium for drug screening in the suspected neonate.

It will be appreciated that the foregoing description is only illustrative of the present invention and that this invention is limited only by the hereinafter appended claims.

I claim:

1. A method for assaying for maternally transferred morphine and cocaine metabolites in a newborn infant which consists essentially of:
   (a) isolating meconium from the newborn infant which possibly contains the transferred metabolites from the mother;
   (b) separating the metabolites from the meconium by mixing with acidic water and then treating the mixture to remove gross particulate matter and to provide an aqueous solution; and
   (c) assaying the solution for the metabolites by an immunoassay using antibodies specific for morphine and cocaine.

2. The method of claim 1 wherein the meconium is fecal.

3. The method of claim 1 wherein the particulate matter is removed by centrifugation.

4. The method of claim 1 wherein the acidic water used to provide the drug metabolites in the solution has a pH between about 1.2 and 4.0.

5. The method of claim 4 wherein hydrochloric acid is used to reduce the pH of the water.

6. The method of claim 1 wherein in addition a lower alkanol solvent is used to extract cannabinoid metabolites from a sample of the meconium and wherein the cannabinoid metabolites in the lower alkanol solvent are assayed.

7. The method of claim 1 wherein the infant is human.

8. The method of claim 1 wherein the meconium is divided into two samples such that one sample is assayed for the morphine and cocaine metabolites and the other sample is mixed with a lower alkanol solvent, then is treated to remove the gross particulate matter to provide a second solution and then the second solution is assayed by an immunoassay using antibodies specific for cannabinoid metabolites.

* * * * *